US009314602B2

(12) United States Patent
Ishikawa et al.

(10) Patent No.: US 9,314,602 B2
(45) Date of Patent: Apr. 19, 2016

(54) MAGNETIC BODY AND DRUG DELIVERY CONTROL DEVICE USING MAGNETIC BODY

(75) Inventors: Yoshihiro Ishikawa, Tokyo (JP);
Haruki Eguchi, Kawasaki (JP);
Masakazu Hara, Yokohama (JP)

(73) Assignees: IHI Corporation, Tokyo (JP); Yoshihiro Ishikawa, Tokyo (JP)

( * ) Notice: Subject to any disclaimer, the term of this patent is extended or adjusted under 35 U.S.C. 154(b) by 199 days.

(21) Appl. No.: 13/518,662

(22) PCT Filed: Dec. 24, 2010

(86) PCT No.: PCT/JP2010/007516
§ 371 (c)(1),
(2), (4) Date: Jun. 22, 2012

(87) PCT Pub. No.: WO2011/077750
PCT Pub. Date: Jun. 30, 2011

(65) Prior Publication Data
US 2012/0259155 A1 Oct. 11, 2012

(30) Foreign Application Priority Data
Dec. 25, 2009 (JP) .................................. 2009-294451

(51) Int. Cl.
*A61M 37/00* (2006.01)
*A61M 31/00* (2006.01)
(Continued)

(52) U.S. Cl.
CPC ............. *A61M 37/00* (2013.01); *A61M 31/002* (2013.01); *H01F 7/0205* (2013.01); *A61B 2019/2257* (2013.01); *A61B 2019/464* (2013.01)

(58) Field of Classification Search
CPC .... A61M 37/00; A61M 31/002; A61K 41/00;
A61K 9/0009; A61K 9/5094; A61K 9/515;
A61K 9/0085; A61K 47/36; A61K 47/34;
A61K 47/48861; A61H 2201/10; A61H 39/00;
A61N 2/002
USPC ................ 600/9–15; 335/209, 219, 296, 302;
128/899
See application file for complete search history.

(56) References Cited

U.S. PATENT DOCUMENTS 1,726,349 A * 8/1929 Hartsough ....................... 600/11
3,197,678 A * 7/1965 Jaroslav ........................ 335/209
(Continued)

FOREIGN PATENT DOCUMENTS

JP 50-049698 A 5/1975
JP 63-289906 A 11/1988
(Continued)

OTHER PUBLICATIONS

Jim Klostergaard et al., "Magnetic vectoring of magnetically responsive nanoparticles within the murine peritoneum" Journal of Magnetism and Magnetic Materials, 311 (2007) 330-335.

*Primary Examiner* — Navin Natnithithadha
*Assistant Examiner* — Kaylee Wilson
(74) *Attorney, Agent, or Firm* — Volpe and Koenig, P.C.

(57) ABSTRACT

A magnetic body may be suitably applied to a drug delivery system using magnetism. Furthermore, a drug delivery control device allows the magnetic body to be suitably applied to drug delivery. The magnetic body includes a magnet and a cover part attached to an edge of the magnet. The cover part is composed of a material with high magnetic permeability, and a ratio of a length to a radius of the cover part is 10:1 to 7:3. The drug delivery control device includes the magnetic body, a head for supporting the magnetic body and a drive mechanism of the head that causes the head to operate along a projected region formed by the affected area with respect to a surface of a tissue. A magnetic field is applied from the magnetic body to the affected area where a magnetic drug is administered.

11 Claims, 11 Drawing Sheets

(51) Int. Cl.
*H01F 7/02* (2006.01)
*A61B 19/00* (2006.01)

(56) References Cited

U.S. PATENT DOCUMENTS

| | | | | |
|---|---|---|---|---|
| 4,936,305 | A | * | 6/1990 | Ashtiani et al. ............... 607/57 |
| 5,364,404 | A | * | 11/1994 | Jaffe et al. .................... 606/106 |
| 5,651,989 | A | | 7/1997 | Volkonsky et al. |
| 5,782,858 | A | | 7/1998 | Cheng |
| 6,488,615 | B1 | | 12/2002 | Mitchiner et al. |
| 2005/0234286 | A1 | * | 10/2005 | Riehl et al. ..................... 600/9 |
| 2009/0169484 | A1 | | 7/2009 | Eguchi et al. |
| 2009/0216067 | A1 | * | 8/2009 | Lebosse et al. ................ 600/13 |

FOREIGN PATENT DOCUMENTS

| | | |
|---|---|---|
| JP | 63-306506 A | 12/1988 |
| JP | 64-016605 U | 1/1989 |
| JP | 2001-010978 A | 1/2001 |
| JP | 2004-342796 A | 12/2004 |
| JP | 2009-173631 A | 8/2009 |
| WO | 01/76038 A2 | 10/2001 |
| WO | 2007/125676 A1 | 11/2007 |
| WO | WO 2007125676 A1 * | 11/2007 |
| WO | WO 2008106484 A1 * | 9/2008 |

* cited by examiner

MAGNETIC BODY AND DRUG DELIVERY CONTROL DEVICE USING MAGNETIC BODY

FIELD OF THE INVENTION

The present invention relates to a magnet and a drug delivery control device using the magnet, and specifically relates to an invention that guides a magnetic drug to an affected area by magnetism when applying the magnetic drug to a human or an animal.

BACKGROUND OF THE INVENTION

As a drug delivery system for drugs, loading the drugs on carriers, and guiding the drugs to target organs, tissues, or affected areas based on physicochemical or physiological properties of the carriers, is known. Various types of antibodies, microspheres, or magnetic bodies have been studied as carriers.

Out of these, a method for concentrating drugs along with magnetic carriers in affected areas by magnetic fields has been introduced. This method is considered especially effective for highly cytotoxic anti-tumor agents toward normal cells because the delivery method is convenient and the affected areas can be treated directly. (See, for example, Patent Document 1).

Also, the assignees of the present application use compounds that have inherent ferromagnetism without employing magnetic carriers, and propose a system that guides drugs to the target tissue by magnetic fields from outside the body. (See, for example, Patent Document 2).

A magnetism-generating means with high magnetic flux density is desired to guide a drug in the body using magnetic fields from outside the body. For example, a technique of concentrating the magnetic flux density at the peak (magnetic pole) of a magnet is introduced.

In this technique, that the magnetic flux density increased by 20% compared to when the peak is left flat, by forming the shape of the peak of the magnet so that it is a pyramid shape is introduced. (See, for example, Non-Patent Document 1).

PRIOR ART DOCUMENTS

Patent Documents

Patent Document 1: Japanese Laid-Open Patent Application No. 2001-10978
Patent Document 2: Japanese Laid-Open Patent Application No. 2009-173631

Non-Patent Document

Non-Patent Document 1: Jim Klostergaard, James Bankson, Edmond Auzenne, Don Gibson; William Yuill, Charles E. Seeney, 'Magnetic vectoring of magnetically responsive nanoparticles within the murine peritoneum', Journal of Magnetism and Magnetic Materials, 311 (2007) 330-335

SUMMARY OF THE INVENTION

Problem to be Solved by the Invention

Magnets are generally obtained by integrally molding magnetic materials using metal molds. Therefore, there is a difficulty in terms of manufacturing in that a special metal mold needs to be used when forming the peak of a magnet to a particular shape, such as a pyramid shape.

In contrast, when applying a typical permanent magnet in which the peak is flat to a drug delivery system, a problem exists in that the magnetic force decreases at once by merely causing the permanent magnet to move slightly away from the target where the magnetic field is to be applied. In this case, applications will be limited to superficial diseases such as subcutaneous tumor.

Thus, it is desirable to dispose the peak of the magnet as close to the affected area as possible. If this is conducted carelessly, and for example, the magnet touches the body forcefully, pain may be inflicted on the body.

In addition, when the magnet moves away from the affected area, the magnetic flux density applied to the affected area may, for example, become insufficient or may vary, and the amount of drug disposed in the affected area may not be appropriate.

Hence, an object of the present invention is to make drug delivery effective using magnetism, and to provide a magnetic body that may be suitably applied to a drug delivery system using magnetism. Furthermore, another object of the present invention is to provide a drug delivery control device that allows the magnetic body to be suitably applied to drug delivery.

Means for Solving the Problem

The present invention is characterized in that, to achieve the object, the present invention allows magnetic flux to be applied to the affected area through concentration of the magnetic flux emitted from the edge, by merely adding a cover part composed of a material with high magnetic permeability to the edge of an existing magnet without using a special metal mold, and without working the peak of the magnet to a particular shape.

That is, the present invention provides a magnetic body including a magnet; and a cover part attached to an edge of the magnet, the cover part is composed of a material with high magnetic permeability, and a ratio of a length to a radius of the cover part is 10:1 to 7:3.

The material with high magnetic permeability that configures the cover part may include a permalloy. In addition, a peak of the cover part is preferably formed to be tapered, such as a cone or a pyramid (a square pyramid or a triangular pyramid). Thus, a magnetic flux density emitted from the cover part may be increased. Furthermore, the peak of the cover part is preferably formed to be flat or formed to be spherical to alleviate an effect when the peak of the cover part touches a body.

Also, the present invention provides a drug delivery control device that applies a magnetic field from the magnetic body to an affected area where a magnetic drug is administered, the drug delivery control device includes the magnetic body, the magnetic body including the magnet; and the cover part attached to the edge of the magnet, a head for supporting the magnetic body; and a drive mechanism of the head that causes the head to operate along a projected region formed by the affected area with respect to a surface of a tissue.

This drug delivery control device further includes a pressure sensor that detects pressure generated from a peak of the magnetic body to the magnet side. The magnetic body may be configured by concentrating the magnetic flux density at the peak.

Additionally, the drive mechanism of the drug delivery control device may cause the head to advance toward and retreat from the affected area, based on output from the pressure sensor. Thus, by using a detected value from the pressure sensor to control the drive of the magnetic body, the magnetic field with high magnetic flux density may be applied to the affected area with no effect.

In addition, it is preferable for the cover part of the drug delivery control device according to the present invention to be composed of the material with high magnetic permeability, and a ratio of a length to a radius of the cover part to be 10:1 to 7:3. This material with high magnetic permeability may include the permalloy.

Also, the cover part of the drug delivery control device according to the present invention may have a configuration in which the peak is formed to be tapered. In this case, the peak of the cover part may be formed to be flat or may be formed to be spherical.

Effects of the Invention

As described above, a magnetic body that may be suitably applied to a drug delivery system using magnetism may be provided, according to the present invention. Furthermore, a drug delivery control device that allows the magnetic body to be suitably applied to drug delivery, may be provided.

DESCRIPTION OF EMBODIMENTS

Figure 1:
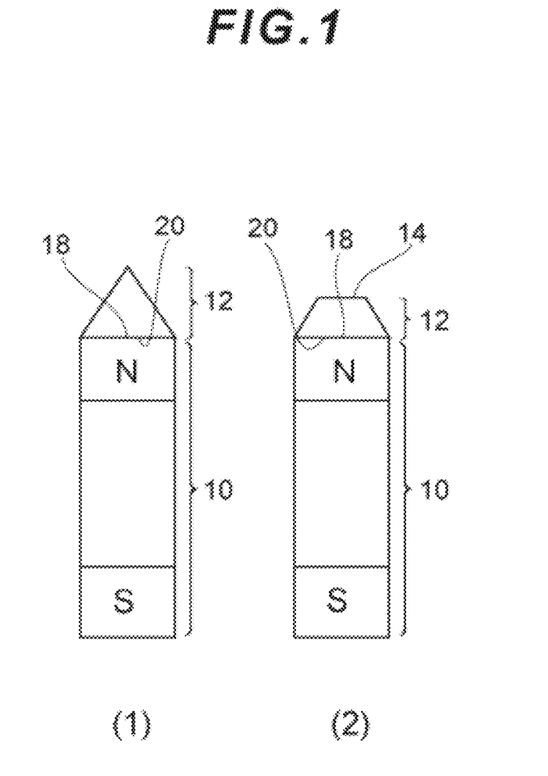
FIG. 1 is a front view of an embodiment of a magnetic body according to the present invention.

Embodiments of the present invention are described below. FIG. 1(1) and FIG. 1(2) show front views of magnetic bodies according to the present invention. FIG. 1(1) is the magnetic body configured by covering an end surface 18 of one end (peak) of a bar-shaped permanent magnet 10 with a triangular cap (cover part) 12 made of a permalloy as viewed from the front. FIG. 1(2) is the magnetic body configured by covering the end surface 18 of the permanent magnet 10 with a trapezoidal cap 12 in which a peak 14 is formed to be flat as viewed from the front. Preferably, a shape of a bottom surface 20 of the cap matches a shape of the end surface 18 of the permanent magnet 10.

A preferable embodiment of the cap 12 with respect to the permanent magnet 10 would have a radius of 30 mm or less when a shape of the cap 12 is a triangle as viewed from the front, and would have a radius of 1 mm to 30 mm when the shape of the cap 12 is a trapezoid as viewed from the front. Also, a height of the cap 12 is 5 mm to 15 mm.

The preferable embodiment of the cap 12 corresponds to a cross-sectional shape in a diametrical direction (in a direction horizontal to the end surface 18) of the permanent magnet 10, such as a cone or the pyramid. The shape of the cap 12 in a diametrical direction matches the cross-sectional shape of the permanent magnet 10. However, the shapes of the cap 12 and the permanent magnet 10 may be different so long as improvement in magnetic flux density is not compromised. The pyramid is not specifically limited to, for example, a triangular pyramid or a square pyramid. In addition, a peak portion of the cone or the pyramid may be formed to be flat. In an embodiment where the peak is formed to be flat, a width of a flat portion of the cap 12 is preferably in a range of 1 mm to 10 mm.

Furthermore, the "radius" or the "diameter" in the present invention refers to a radius or a diameter of a circle to which the permanent magnet 10 and the cap 12 touches internally when the permanent magnet 10 and the cap 12 are pyramids.

Figure 2:
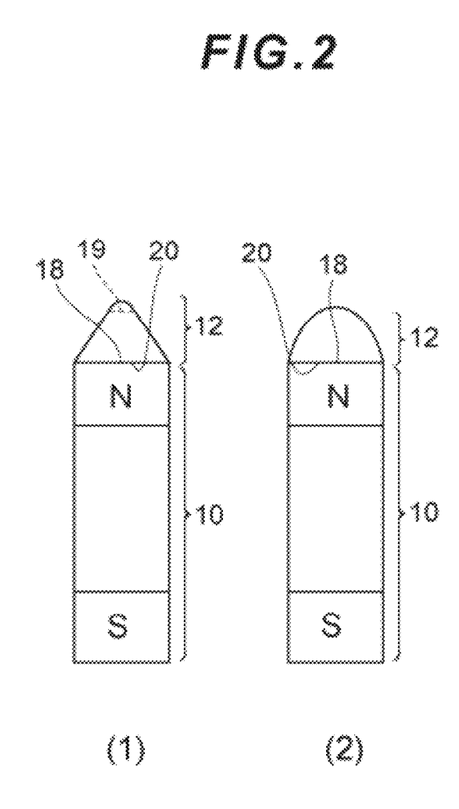
FIG. 2 is a front view of another embodiment of the magnetic body according to the present invention.

Also, FIG. 2(1) and FIG. 2(2) show front views of another embodiment of the magnetic body according to the present invention. FIG. 2(1) is the magnetic body configured by covering the end surface 18 of the bar-shaped permanent magnet 10 with the cap (cover part) 12 made of the permalloy in which the shape of the peak portion is changed from a triangular shape to a round shape as viewed from the front. FIG. 2(2) is the magnetic body configured by covering the end surface 18 of the permanent magnet 10 with an approximately hemispherical cap (cover part) 12 made of the permalloy. Preferably, the shape of the bottom surface 20 of the cap matches the shape of the end surface 18 of the permanent magnet 10.

A preferable embodiment of the cap 12 with respect to the permanent magnet 10 illustrated in this FIG. 2(1) would have a radius of 1 mm to 30 mm at a portion to be a starting point of a round shape 19 of the cap 12. A height from the bottom surface 20 of the cap 12 to the portion to be the starting point of the round shape 19 would be 5 mm to 15 mm. A height from a radius of the round-shaped portion (approximately hemispherical) and the portion to be the starting point of the round shape 19, to a peak of the round shape, is approximately the same as the radius of the portion to be the starting point of the round shape 19. Moreover, a peak portion of the cap 12 is not limited to the approximately hemispherical shape as illustrated in FIG. 2(1), and may be a curved surface that configures a part of a given spherical surface.

In addition, a preferable embodiment of the cap 12 with respect to the permanent magnet 10 illustrated in FIG. 2(2) would have a radius and a height of the hemisphere of the cap 12 approximately the same as a radius of the end surface 18. Furthermore, the cap 12 is not limited to the approximately hemispherical shape as illustrated in FIG. 2(2). The cap 12 may have a radius of 1 mm to 30 mm at the bottom surface 20, the cap 12 may have a height of 5 mm to 15 mm, and may be a curved surface that configures a part of a given spherical surface.

The permanent magnet 10 is, for example, a neodymium permanent magnet. A material with high magnetic permeability (for example, initial permeability $\mu_i$ is 4,500 or greater and 60,000 or less, and maximum permeability $\mu_m$ is 45,000 or greater and 180,000 or less) is, for example, the permalloy. As one example, a surface inductive flux of the neodymium permanent magnet (N50, a bar magnet 20 mm in diameter× 500 mm in length: by Shin-Etsu Chemical Co., Ltd.) is 630 mT. However, when this is covered with the conical permalloy cap, the magnetic flux density increased by 18% and became 788 mT. The cap 12 is magnetically adhered firmly to the end surface 18 of the permanent magnet 10.

Thus, by attaching the cap 12 composed of the material with high magnetic permeability to the peak of the permanent magnet 10, reducing a diameter of a peak side of the cap 12 as illustrated in FIG. 1(1) and FIG. 1(2), and emitting a magnetic line of force emitted from a surface of the permanent magnet 10, from the peak of the cap 12 in a vicinity of an affected area, without the magnetic line of force being attenuated in the material with high magnetic permeability when positioning the peak of the permanent magnet 10 in the vicinity of the affected area, it is possible to increase the magnetic flux density applied to the affected area.

Figure 3:
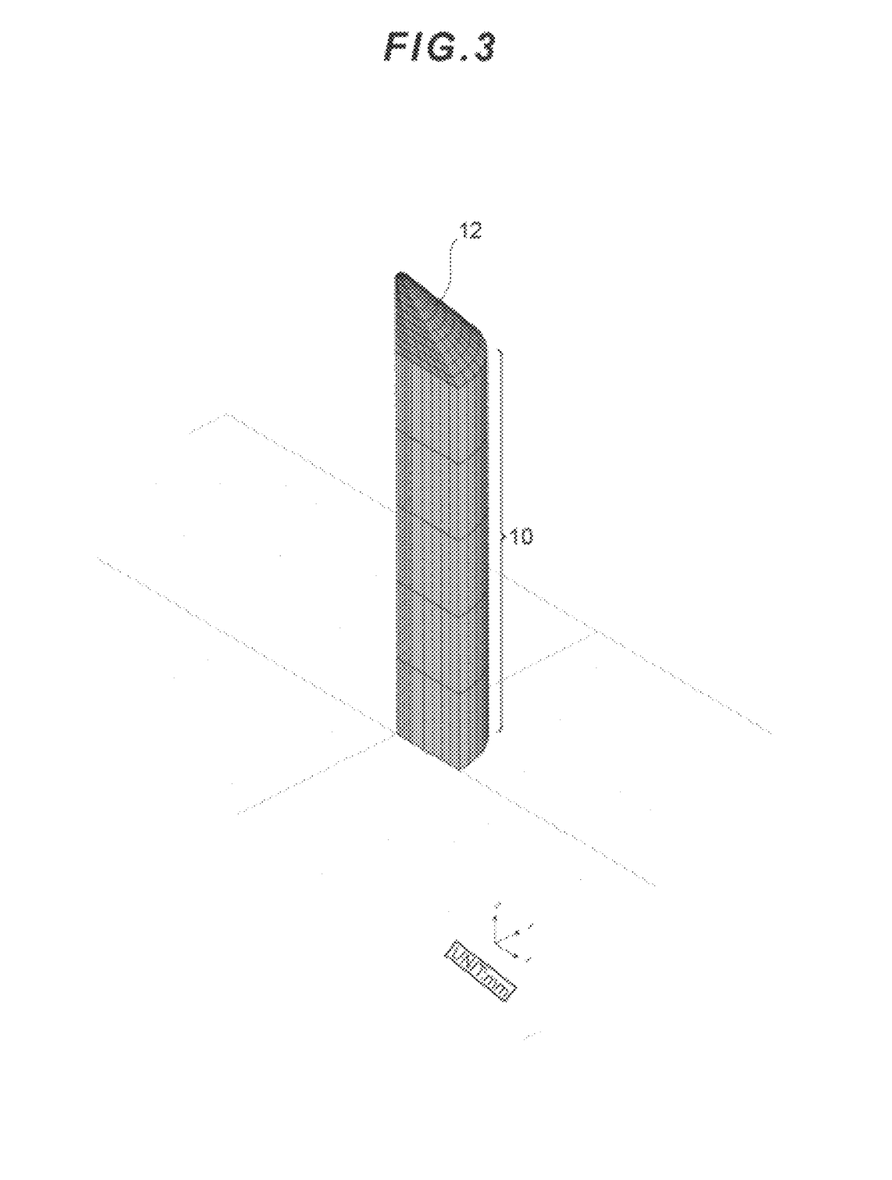
FIG. 3 is a model diagram of a magnet when simulating a magnetic flux density.

Next, a preferable shape of the cap 12, which is the cover part added to one end of the permanent magnet 10, is analyzed with electromagnetic field analysis software (JMAG (Registered Trademark) (by The Japan Research Institute, Limited, "Studio" or "JMAG-ELii") that is industry-standard software. The permanent magnet 10 is presumed to be the bar magnet, N50 (20 mm in diameter×500 mm in length) by Shin-Etsu Chemical Co., Ltd. It is presumed that the cap 12 made of the permalloy is disposed on the peak of the permanent magnet 10. A computation model in this case is shown in FIG. 3.

A configuration in which the permanent magnet 10 is cut into fours (a projected bottom surface is cut based on an axis) from the peak is employed as the computation model of the permanent magnet 10. A number of contact points is 7,839, and a number of elements is 6,650 in an analysis mesh. First, the magnetic flux density of only the permanent magnet 10 (in which the cap 12 is not disposed, and the end surface 18 is flat) is analyzed. This result is shown in FIG. 4.

Figure 4:
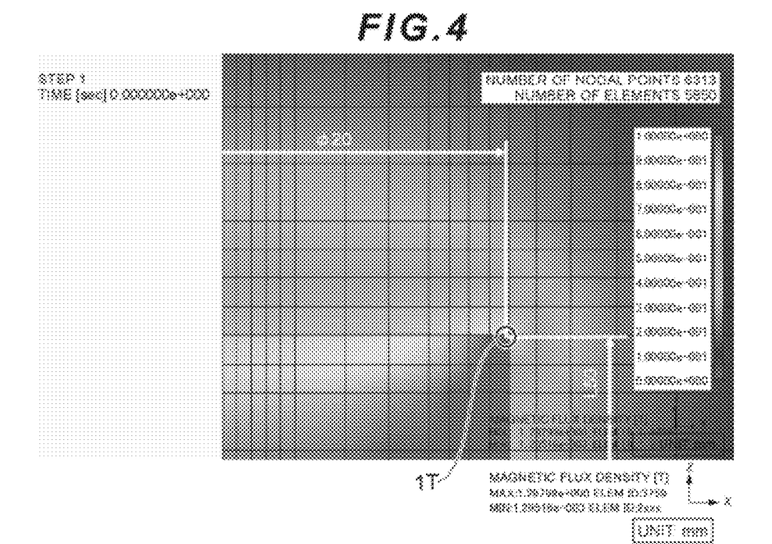
FIG. 4 is a first simulation result of the magnetic flux density.

It is inferred from FIG. 4 that the magnetic flux density decreases to 0.6 T at a center of the peak portion while the magnetic flux density of an edge portion in the peak portion of the permanent magnet 10 (an edge in the diametrical direction) is 1 T.

Next, the magnetic flux density is calculated by varying the shape of the conical permalloy, which is the cap 12 disposed on the peak of the permanent magnet 10, so that a dimension in a lengthwise direction (a height) of the bar magnet is varied from 5 mm to 15 mm, and a radius of a region at which the peak is cut to be flat, is varied from 5 mm to 1 mm.

Figure 5:
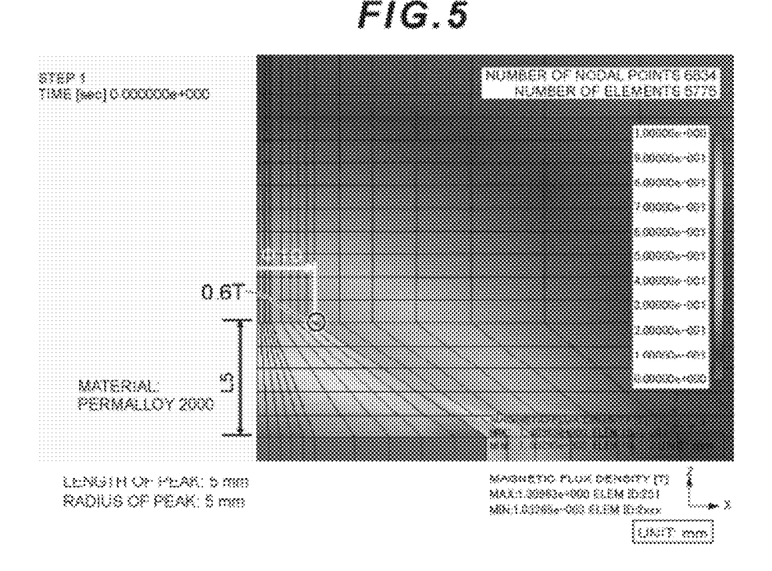
FIG. 5 is a second simulation result of the magnetic flux density.

FIG. 5 is an analysis result when the dimension of the cap 12 (permalloy) in the lengthwise direction (the height) is 5 mm, and the radius of the peak is 5 mm. It is inferred from FIG. 5 that a surface inductive flux of the cap 12 is 0.6 T.

Figure 6:
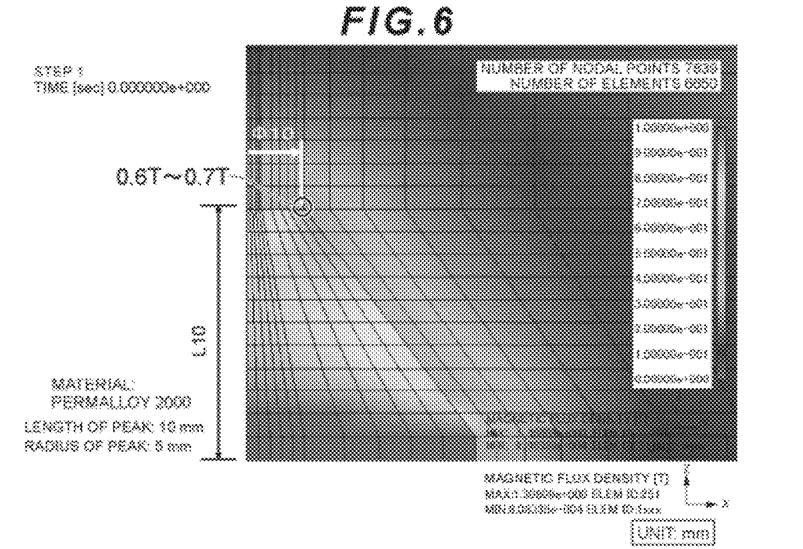
FIG. 6 is a third simulation result of the magnetic flux density.

FIG. 6 is an analysis result when the dimension of the cap 12 (permalloy) in the lengthwise direction (the height) is 5 mm, and the radius of the peak is 5 mm. It is inferred from FIG. 6 that the surface inductive flux of the peak of the cap 12 is 0.6 to 0.7 T.

Figure 7:
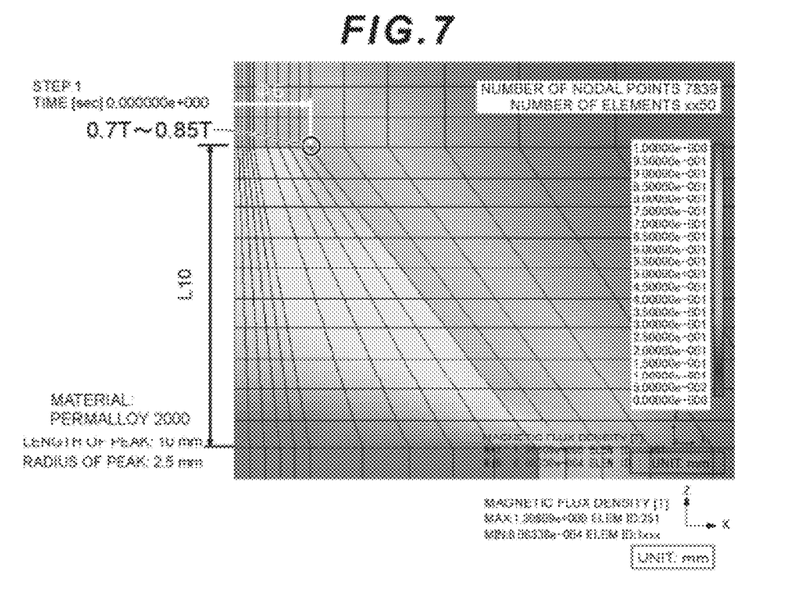
FIG. 7 is a fourth simulation result of the magnetic flux density.

FIG. 7 is an analysis result when the dimension of the cap 12 (permalloy) in the lengthwise direction (the height) is 10 mm, and the radius of the peak is 2.5 mm. It is inferred from FIG. 7 that the surface inductive flux of the peak of the cap 12 is 0.7 to 0.85 T.

Figure 8:
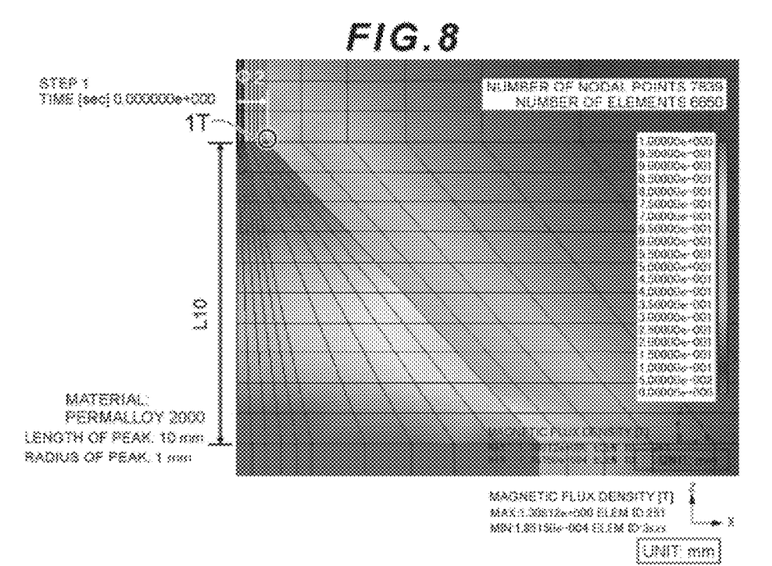
FIG. 8 is a fifth simulation result of the magnetic flux density.

FIG. 8 is an analysis result when the dimension of the cap 12 (permalloy) in the lengthwise direction (the height) is 10 mm, and the radius of the peak is 1 mm. It is inferred from FIG. 8 that the surface inductive flux of the peak of the cap 12 is approximately 1 T, and is approximately equivalent to a value of a maximum magnetic flux density of an edge of the surface of the permanent magnet.

Figure 9:
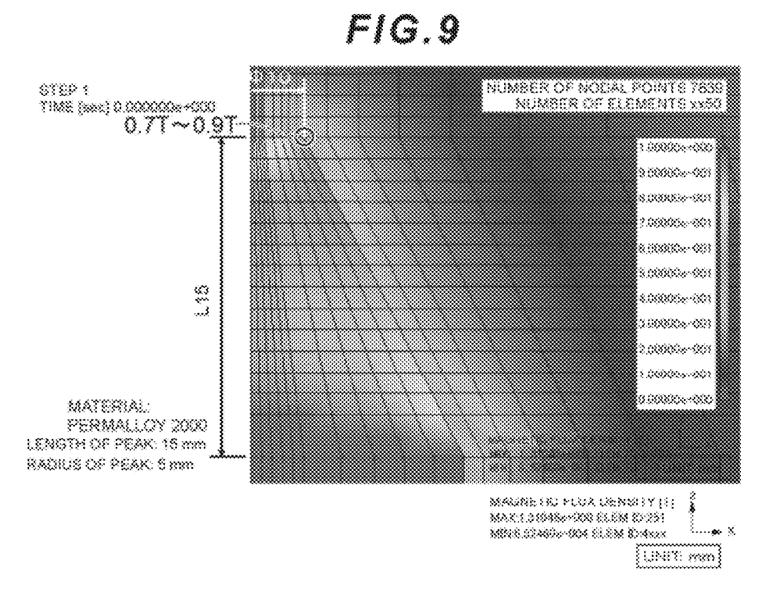
FIG. 9 is a sixth simulation result of the magnetic flux density.

FIG. 9 is an analysis result when the dimension of the cap 12 (permalloy) in the lengthwise direction (the height) is 15 mm, and the radius of the peak is 5 mm. It is inferred from FIG. 9 that the surface inductive flux of the peak of the cap 12 is approximately 0.7 to 0.9 T.

From the above, an especially preferable value in improving the surface inductive flux of a shape size of the cap 12 is desirably 10 mm in dimension in the lengthwise direction of the permanent magnet 10, 1 mm in the radius of the peak, and 10:1 to 7:3 in a ratio of the length to the radius of the cap 12, so long as the cap 12 is disposed on (covers) the edge of the permanent magnet 10.

Figure 10:
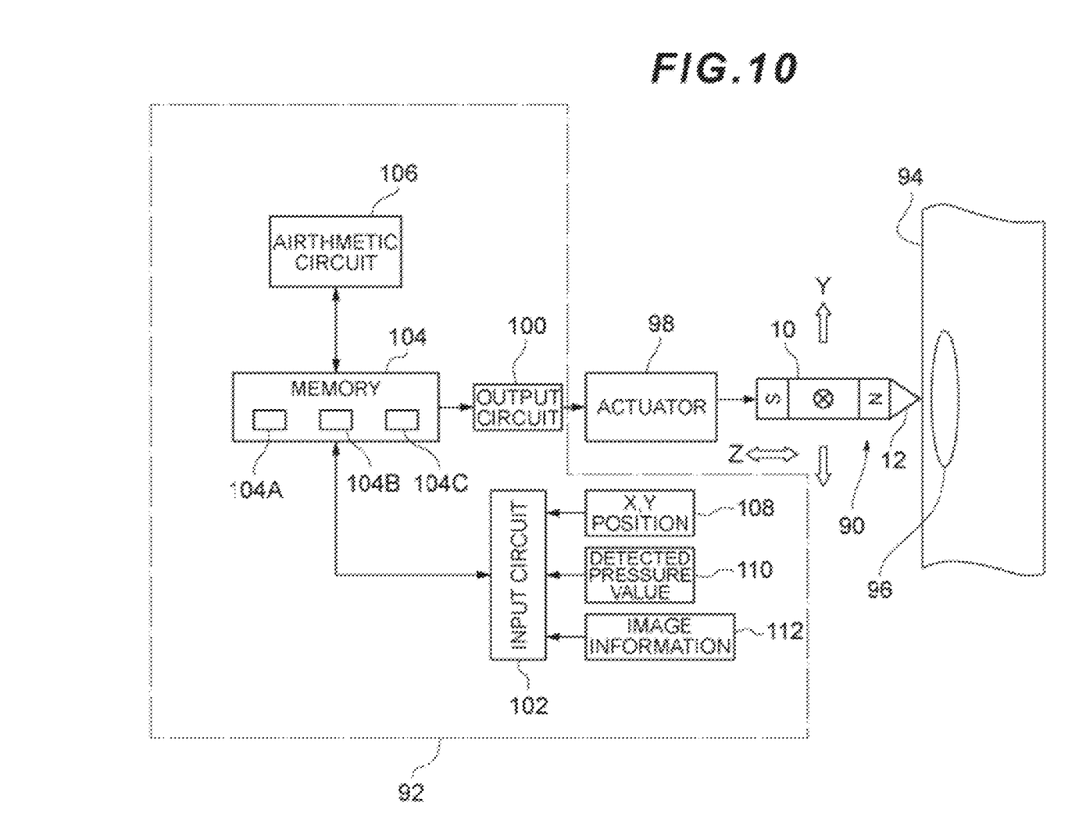
FIG. 10 is a block diagram illustrating a system configuration of a drug delivery control device according to the present invention.
Figure 11:
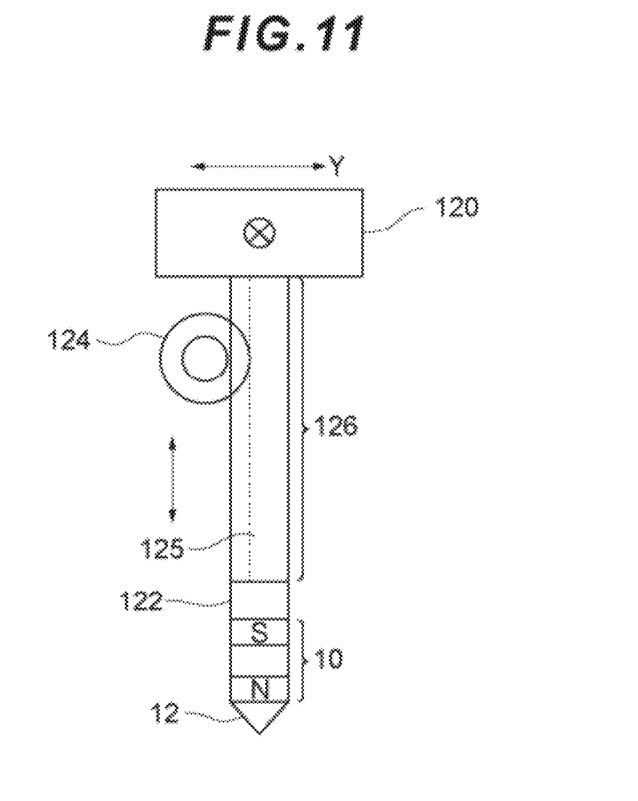
FIG. 11 is a front view illustrating a detailed configuration of a head including the magnet.

An embodiment of a drug delivery control device using the aforementioned magnet is described below. FIG. 10 is a hardware block diagram of a whole system, and FIG. 11 is an enlarged front view of the magnet and a head that includes a mechanism for supporting the magnet. In FIG. 10, an illustration of the support mechanism is omitted, and only the magnet is illustrated as the head.

The drug delivery control device illustrated in FIG. 10 functions as a medical magnetism application device, and includes a head 90 that includes the permanent magnet 10 where the permalloy cap 12 is attached to the peak, and a support mechanism 126 that supports this permanent magnet 10 (see, FIG. 11), an actuator 98 that moves the head 90 in a three-dimensional direction, and a control system 92 that controls this actuator 98.

The control system 92 is constituted from a computer system, and includes a memory 104, an airthmetic circuit 106, an input circuit 102, and an output circuit 100. A diagnostic image information storage portion 104A, a control program storage portion 104B, a control data storage portion 104C exist in the memory 104. Although not illustrated, a control information output circuit exists in the control system 92.

An XY position information 108 from an XY position sensor of the head, a detected value 110 from a pressure sensor, and diagnostic image information 112 of an affected area region 96 (for example, a cancer lesion) in a body 94 is provided to the input circuit 102. The airthmetic circuit 106 outputs a drive control signal to the actuator 98 via the output circuit 100 to cause the head 90 to drive in an XYZ direction.

The control program storage portion 104B stores the diagnostic image information 112 in the diagnostic image information storage portion 104A, recognizes two-dimensional information and three-dimensional information of the affected area region 96, and determines a trajectory at which the head 90 is to scan the affected area region 96, based on this recognition result.

The trajectory at which to scan is a stroke when reciprocating the head in the region along a projected region of the affected area region that appears on a surface of a tissue.

The airthmetic circuit 106 executes the control program storage portion 104B, reads control data for determining the scan trajectory from the control data storage portion 104C, and in addition reads a position data of the affected area region 96 from the diagnostic image information storage portion 104A, and determines an expected trajectory of the head 90 based on these read data.

Next, the airthmetic circuit 106 generates the drive signal for the actuator 98 based on the expected trajectory, and outputs this to the actuator 98 from the output circuit 100. A diagnostic image is generated by a diagnostic imaging device such as MRI.

A CCD camera may be used as the diagnostic imaging device for cancer on a surface of the body such as carcinoma cutaneum.

The control program storage portion 104B includes a program for identifying the affected area region 96 from the diagnostic image. The airthmetic circuit 106 detects a location of the affected area from the diagnostic image by executing the program using the diagnostic image information 112. The determination of the location of the affected area region from the diagnostic image information may be executed at an image processing apparatus side.

FIG. 11 shows a schematic view of the head including the permanent magnet 10 and the support mechanism 126 of the permanent magnet 10. The peak of the permanent magnet 10 at an affected area side is covered with the aforementioned conical or pyramidal cap 12 composed of the permalloy. A base end side of the bar-shaped permanent magnet 10 is attached to the support mechanism 126. A pressure sensor 122 exists between the permanent magnet 10 and the support mechanism 126.

Furthermore, the peak of the cap 12 is formed to be a small flat surface and a small spherical surface in the present embodiment so that it is safe for the peak of the cap 12 to touch the body. The support mechanism 126 is configured by a rack 125 that advances and retreats in the lengthwise direction by a pinion 124.

An XY direction slide drive mechanism 120 for moving the permanent magnet in an XY direction is provided at a base end of the rack 125. In addition, a Z direction slide drive mechanism that causes the head 90 to advance and retreat with respect to the affected area region 96 by the rack 125 and the pinion 124, is configured.

The XY direction slide drive mechanism 120 is configured by an XY drive table. This XY direction slide drive mechanism 120 includes a first sensor that detects a position in the XY direction of the head 90, and the Z direction slide drive mechanism includes a second sensor for indirectly detecting a position in a Z direction of the permanent magnet 10. Furthermore, the aforementioned pressure sensor 122 is equivalent to the second sensor mentioned here.

Figure 12:
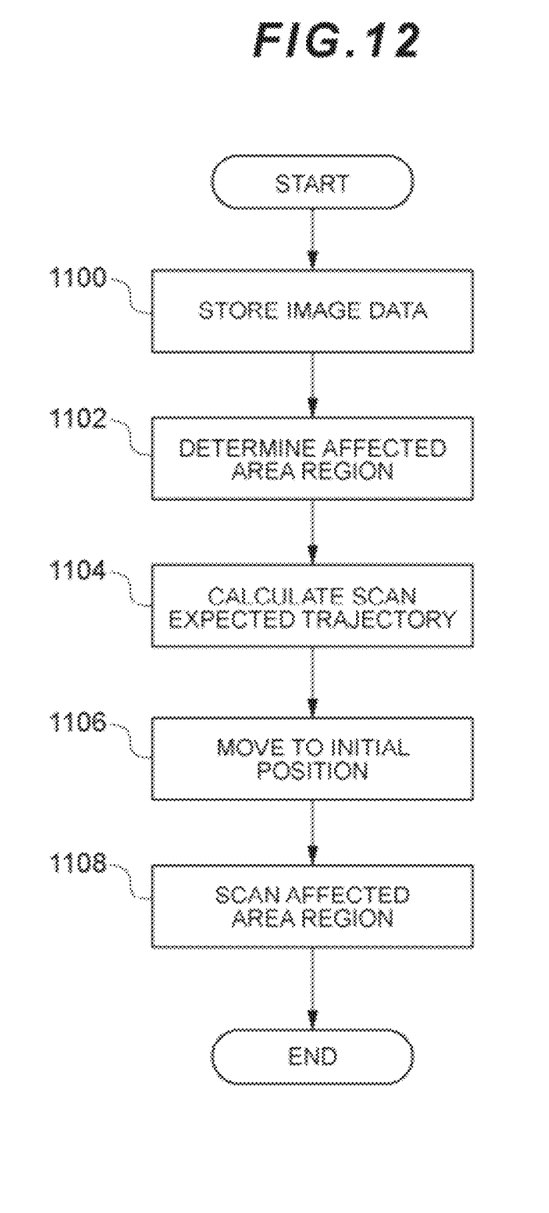
FIG. 12 is a flowchart illustrating an operation of the drug delivery control device of FIG. 10.

An operation of the drug delivery control device is described below based on a flowchart of the airthmetic circuit 106 in which a control program is executed. This flowchart is shown in FIG. 12.

First, the airthmetic circuit 106 stores the diagnostic image information 112 from the diagnostic imaging device in the diagnostic image information storage portion 104A of the memory 104 (step 1100).

Next, the airthmetic circuit 106 determines the region at which the affected area exists, from the diagnostic image information, and stores this in the control data storage portion 104C (step 1102). Furthermore, this region may be identified by a three-dimensional position data in the XYZ direction, or a two-dimensional position data in XY of the affected area that exists with respect to body tissue.

Next, the airthmetic circuit 106 calculates a scan expected trajectory of the head 90, based on the affected area region 96 (step 1104). The airthmetic circuit 106 subsequently moves the head 90 to an initial position in the XY direction (step 1106). The initial position is set by the control program accordingly. For example, the initial position may be a center of a shape, an area, and a volume of the affected area, based on the shape, the area, and the volume of the affected area.

The airthmetic circuit 106 subsequently causes the pinion 124 to rotate, and causes the head 90 to advance slowly toward the affected area side. When the peak of the cap 12 touches the surface of the body or the surface of the tissue at which the affected area exists, the pressure sensor 122 detects contact pressure. The airthmetic circuit 106 stops a progress of the head in the Z direction, causes the head to slightly retreat from or slightly advance to the affected area, and moves the XY slide mechanism from the initial position to an end-point position along the expected trajectory of the scan, according to the contact pressure (step 1108).

Furthermore, a best position of the permanent magnet 10 with respect to the affected area is a position where the peak of the cap 12 slightly touches the affected area. It is not preferable for the permanent magnet 10 to press an affected tissue more than is necessary, whereas it is not preferable for the permanent magnet 10 to move away from the affected area when it is still difficult to provide a required magnetic flux density to the affected tissue. The airthmetic circuit 106 detects the XY position information and a signal from the pressure sensor 122 regularly, and feedback controls a position of the head in the XYZ direction.

Additionally, the airthmetic circuit 106 checks the detected value of the pressure sensor 122 periodically. When pressure is not detected, the head 90 is moved to the affected area region 96 slowly, and the head 90 is positioned so that it is positioned most suitably with respect to the affected area region 96. In addition, when pressure exceeds a given value, a position of the head 90 in the Z direction may be corrected so that the position of the head 90 becomes most suitable, by causing the head 90 to retreat slightly from the affected area region 96.

Cases of the affected areas mainly deal with cancer. Well-known magnetic drugs (including a compound that has inherent magnetism, and a drug that uses magnetic carriers) is applied by oral administration, injection, or infusion. The drug is trapped in the affected area region 96 by magnetic flux from the peak of the permanent magnet 10.

Figure 13:
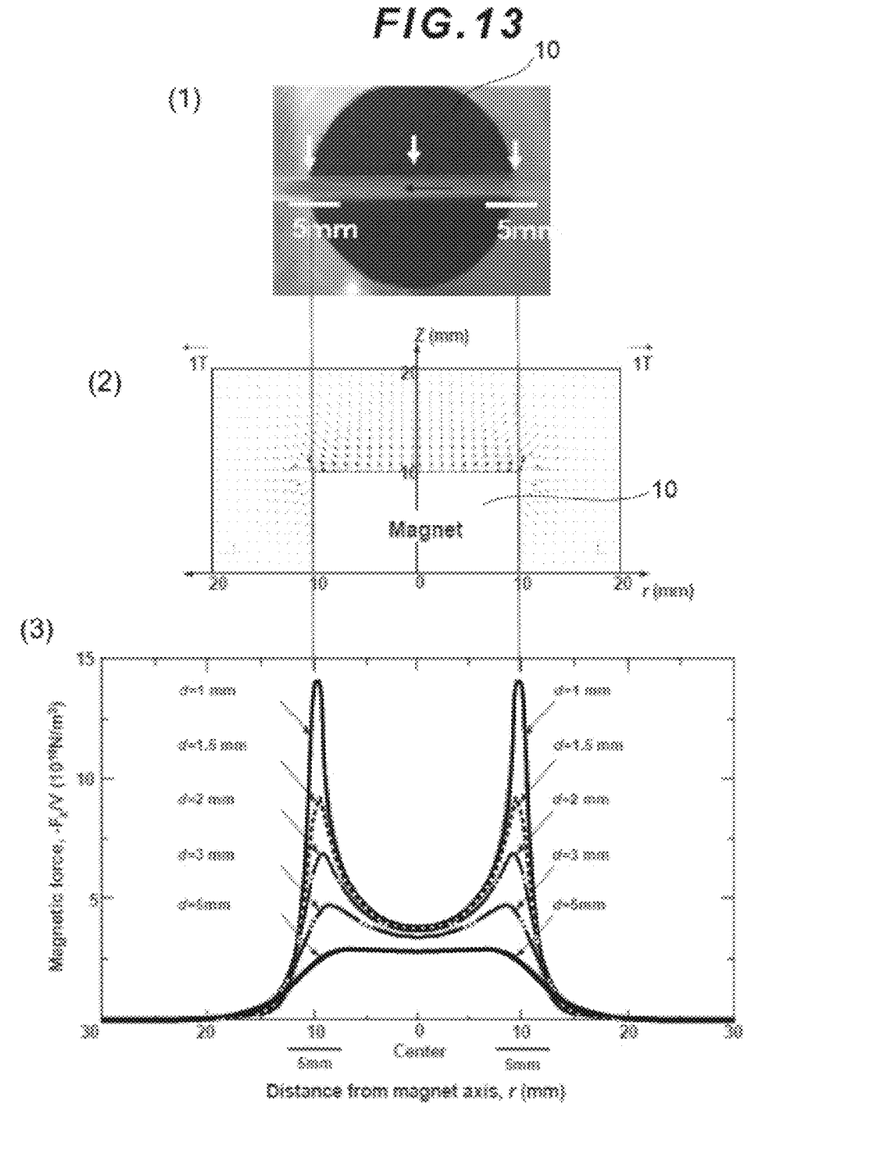
FIG. 13 is a figure for illustrating a magnetic effect of a circular magnet to an iron-salen complex compound.

This is demonstrated by an example described below. FIG. 13(1) is a photograph showing an embodiment in which an iron-salen complex compound dissolved in water, expressed by the following Chemical Formula (I), is circulated inside a glass tube over the permanent magnet in which the shape of the end surface is circular. Iron-salen complexes are trapped in regions of 5 mm indicated by arrows on both sides of the circular magnet, in the diametrical direction.

[CI]

(I)

The permanent magnet 10, 20 mm in diameter×150 mm in length was used. A velocity of flow of a solution is 100 mm/sec, an inside diameter of the glass tube is 1.3 mm. A concentration of the compound of (I) specified above is 10 mg/ml. Furthermore, the iron-salen complex was manufactured by the method disclosed in Japanese Laid-Open Patent Application No. 2009-173631.

FIG. 13(3) shows magnetic distribution of Chemical Formula (I) by spherical approximation. A horizontal axis is a distance of the permanent magnet 10 in a radial direction, and a vertical axis is magnetic force. "d" is a length of a space generated between the permanent magnet 10 and the glass tube. For example, d=1 mm represents that the space between the permanent magnet 10 and the glass tube is precisely 1 mm.

Figure 14:
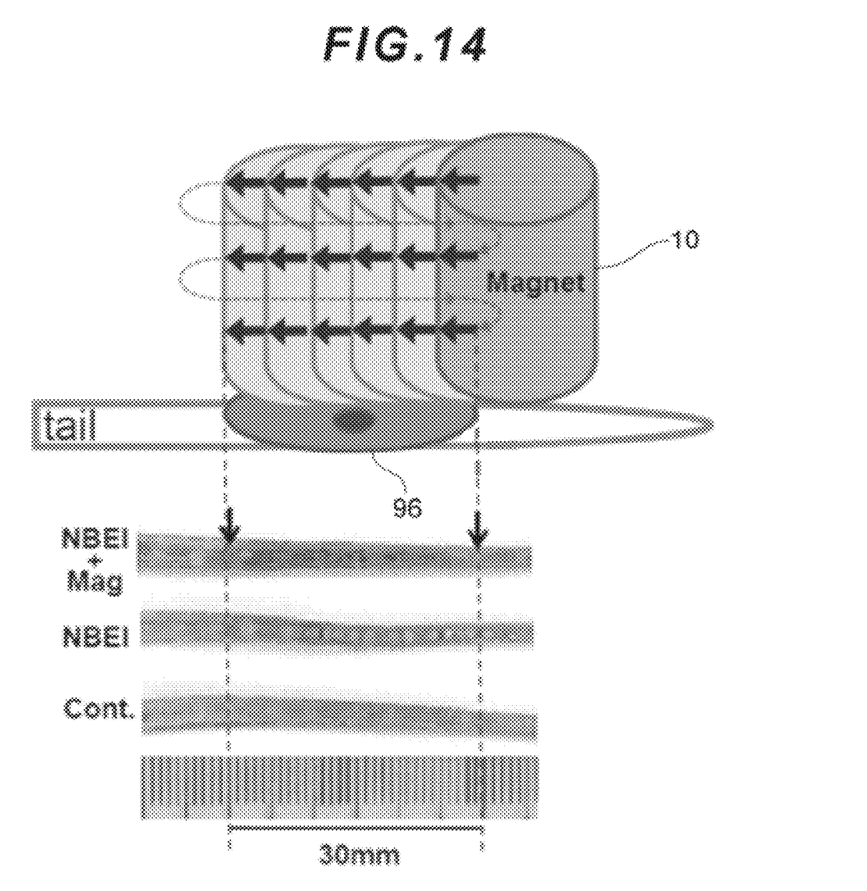
FIG. 14 is a figure for illustrating the magnetic effect when disposing an iron-salen complex in a tail of a rat, and reciprocating the magnet over a region of a tumor.

As illustrated in FIG. 13(1) to FIG. 13(3), the permanent magnet 10 was caused to reciprocate with respect to the affected area region 96 as indicated by the arrows in FIG. 14 because magnetic field strength and magnetic flux density at the edge of the permanent magnet 10 in the diametrical direction is high. This is the same when the cap 12 in which the peak is formed to be sharp, is affixed to the end surface of the permanent magnet 10. Moreover, FIG. 14 illustrates a scheme of a behavior of the permanent magnet 10.

Next, after injecting the compound of Chemical Formula (I) into a tail vein of a rat, the magnet is placed over the tail of the rat so that a left end of the end surface of the magnet is placed over a right end portion of the affected area region, and is left to rest for ten minutes. The magnet is subsequently moved 5 mm to the left, and is likewise left to rest for ten minutes. This is repeated as indicated by the arrows in FIG. 14.

Next, an effect of the iron-salen complex on a melanoma growth in a mouse, was checked by using a staining technique. Melanoma was established in a mouse tail in vivo by local grafting of a cultured melanoma cell (Clone M3 melanoma cell).

The iron-salen complex (50 mg/kg) was administered intravenously via the tail vein once a day for 14 days. The magnetic field was locally applied by use of a commercially available bar magnet (630 mT, a cylindrical neodymium magnet, 150 mm in length and 20 mm in diameter). A site of the melanoma was gently touched by the bar magnet for three hours immediately after injection of the salen complex.

The bar magnet was moved as illustrated in FIG. 14. Twelve days after an initial injection of the salen complex, an extension of the melanoma was evaluated by assessing an area of melanoma pigmentation.

Existence of a metal-salen complex in the tissue may be identified by a blue stain (Trypan blue test). NBEI+ Mag shown in FIG. 14 is a result of the permanent magnet 10 being applied to the salen complex. NBEI is a result of only the metal-salen complex being applied, without applying the permanent magnet 10. Cont is a result when physiological saline, which does not include iron salen, is injected into the tail vein.

Thus, by administering a metal-salen complex compound into the body, and moving the permanent magnet 10 over a tumor region, it is possible to retain the metal-salen complex in this tumorous tissue so that the tumor region that has proliferated extensively, is covered. Furthermore, that the iron-salen complex, and a combination of the iron-salen complex and the magnetic field bring about an antitumor effect, and that the effect of the latter is predominantly superior compared to the former, is as the inventors have reported in Japanese Laid-Open Patent Application No. 2009-173631.

The embodiments and the example described above do not limit the scope of the present invention. For example, the shape of the magnet, the shape of the cover part, its material, and the configuration of the drug delivery control device may be modified accordingly by a person skilled in the art.

Also, the magnetic drug is not limited to the aforementioned magnetic drug. For example, those disclosed in Japanese Laid-Open Patent Application No. 2009-173631 and Japanese Patent Application No. 2009-177112 may be applied to the present invention.

DESCRIPTION OF THE REFERENCE NUMERALS 10 permanent magnet
12 Cover part (cap)
14 peak of the cap
18 end surface
90 head
96 affected area region
98 actuator
104 memory
106 airthmetic circuit
120 XY direction slide drive mechanism
122 pressure sensor
124, 126 Z direction slide drive mechanism

The invention claimed is:

1. A magnetic body comprising:
a neodymium magnet having a length, center, and longitudinal axis along the length and the center of the magnet; and
a cover part attached to an edge of the magnet, wherein:
the cover part is composed of a material with high magnetic permeability that includes a permalloy,
a ratio of a length to a radius of the cover part is 10:1 to 7:3,
a side surface of the cover part in a lengthwise direction is formed to be tapered toward a peak of the cover part centered on or about the longitudinal axis, the peak having a rounded shape, which extends from a starting point along the longitudinal axis of the cover part to an upper-most point along the longitudinal axis of the cover part,
the cover part has a bottom surface that is adjacent the edge of the neodymium magnet, and
a radius of the cover part at the starting point is between 1 mm and 30 mm, a height from the bottom surface of the cover part to the starting point is between 5 mm and 15 mm, and a height of the peak from the starting point to the upper-most point is approximately the same as the radius of the cover part at the starting point.

2. A drug delivery control device comprising:
a magnetic body, the magnetic body including:
a neodymium magnet having a length, center, and longitudinal axis along the length and the center of the magnet; and
a cover part attached to an edge of the magnet, wherein:
the cover part comprises a material with high magnetic permeability that includes a permalloy,
a ratio of a length to a radius of the cover part is 10:1 to 7:3, and
a side surface of the cover part in a lengthwise direction is tapered toward a peak of the cover part centered on or about the longitudinal axis, the peak having a rounded shape, which extends from a starting point along the longitudinal axis of the cover part to an upper-most point along the longitudinal axis of the cover part,
the cover part has a bottom surface that is adjacent the edge of the neodymium magnet, and
a radius of the cover part at the starting point is between 1 mm and 30 mm, a height from the bottom surface of the cover part to the starting point is between 5 mm and 15 mm, and a height of the peak from the starting point to the upper-most point is approximately the same as the radius of the cover part at the starting point;

a head including a support mechanism supporting the magnet of the magnetic body; and an XY direction slide drive mechanism and a Z direction slide drive mechanism connected to the support mechanism of the head that causes the head to operate along a projected region formed by an affected area with respect to a surface of a tissue, wherein the drug delivery control device applies a magnetic field from the magnetic body to the affected area where a magnetic drug is administered.

3. The drug delivery control device according to claim 2, comprising: a pressure sensor detecting pressure generated from a peak of the magnetic body to a side of the magnet, wherein the magnetic body concentrates a magnetic flux density at the peak.

4. The drug delivery control device according to claim 3, wherein the Z direction drive mechanism causes the head to advance toward and retreat from the affected area based on output from the pressure sensor.

5. The drug delivery control device of claim 2, wherein the Z direction slide mechanism includes a rack along the support mechanism and a pinion, the rack is configured to advance or retreat upon rotation of the pinion, and to cause the head to advance or retreat.

6. The drug delivery control device of claim 5 further comprising a pressure sensor between the magnet and the support mechanism.

7. The drug delivery control device of claim 5, wherein the drive mechanism is configured to reciprocate over the affected area.

8. The drug delivery control device of claim 5, wherein the XY drive mechanism is configured to reciprocate over the affected area by positioning the magnetic body toward one side of the affected area for a first period, moving the magnetic body to another side of the affected area for a second period of time, and repeating the positioning and moving steps.

9. The drug delivery control device of claim 8, wherein the first period is ten minutes and the second period is ten minutes.

10. The drug delivery control device of claim 2 further comprising an arithmetic circuit configured to store diagnostic image information, determine a region where the affected area exists from the diagnostic image information, and calculates a scan trajectory for the head to the affected area.

11. The drug deliver control device of claim 10, wherein the arithmetic circuit moves the head to an initial position in the XY direction, then causes the head to move in the Z direction toward or away from the affected area, and then moves the head from the initial position in the XY direction to an end-point position along the expected trajectory of the scan.

* * * * *